United States Patent [19]

Guirguis

[11] Patent Number: 5,215,102
[45] Date of Patent: Jun. 1, 1993

[54] CAPILLARY BLOOD ANTIGEN TESTING APPARATUS

[75] Inventor: Raouf A. Guirguis, Rockville, Md.
[73] Assignee: La Mina Ltd., Rockville, Md.
[21] Appl. No.: 782,626
[22] Filed: Oct. 25, 1991
[51] Int. Cl.$^5$ .............................................. A61B 5/00
[52] U.S. Cl. ............................ 128/771; 422/101
[58] Field of Search ............ 128/760, 771; 604/317, 604/318; 422/101, 102; 435/296

[56] References Cited

U.S. PATENT DOCUMENTS

| | | | |
|---|---|---|---|
| 4,040,791 | 8/1977 | Kuntz | 23/259 |
| 4,458,020 | 7/1984 | Bohn et al. | 435/296 |
| 4,473,530 | 9/1984 | Villa-Real | 422/58 |
| 4,557,274 | 12/1985 | Cawood | 128/760 |
| 4,573,983 | 3/1986 | Annis | 604/332 |
| 4,789,638 | 12/1988 | Kramer et al. | 436/111 |
| 4,865,813 | 9/1989 | Leon | 422/101 |
| 4,953,561 | 9/1990 | Guirguis | 128/771 |
| 4,960,130 | 10/1990 | Guirguis | 128/760 |
| 4,961,432 | 10/1990 | Guirguis | 128/760 |
| 5,003,988 | 4/1991 | Guirguis | 128/771 |
| 5,016,644 | 5/1991 | Guirguis | 128/771 |
| 5,022,411 | 6/1991 | Guirguis | 128/771 |
| 5,024,237 | 6/1991 | Guirguis | 128/760 |

FOREIGN PATENT DOCUMENTS

| | | |
|---|---|---|
| 0304000 | 2/1989 | European Pat. Off. . |
| 3241922A1 | 5/1984 | Fed. Rep. of Germany . |
| WO84/02004 | 5/1984 | PCT Int'l Appl. . |

Primary Examiner—Max Hindenburg
Attorney, Agent, or Firm—John S. Hale

[57] ABSTRACT

A fluid testing apparatus comprising a housing, a structure defining a well located in housing, a container rotatably mounted in the housing and positioned over the well. The container has a housing with a fluid flow aperture in which a filter is mounted to filter fluid passing therethrough into the well. A capillary ligand test assembly is secured to said container housing and comprises a capillary tube, a membrane strip mounted in the capillary tube and absorbent material mounted in the capillary tube adjacent the membrane strip. The membrane strip is divided into a testing zone and a control zone provided with designated ligands to capture other specific predetermined ligands.

64 Claims, 9 Drawing Sheets

CAPILLARY BLOOD ANTIGEN TESTING APPARATUS

BACKGROUND OF THE INVENTION

The present invention is directed to medical and laboratory fluid specimen collecting and testing apparatus, and more specifically to an apparatus for detecting the presence of specific antigens in biological fluids.

It is generally necessary in diagnosing and testing for many diseases to collect biological fluids from a patient, e.g., sputum, blood, pleural, cavity and peritoneal cavity fluids for analysis. It is important during the collection handling of biological fluid specimens that the potential of specimen contamination and the spread of any infection from the specimen be minimized. In addition there is also the potential for specimen damage during the collection process as well as the potential for destruction of certain components of the specimen because the testing apparatus does not screen fluids or causes mixing of different fluid components which will negate the test results or result in false data being obtained when the specimen is tested.

In the health-care industry, diagnostic testing of blood has become routine, with physicians expecting and demanding a wide variety of specialized tests on patients' samples to support their diagnoses. To satisfy this ever increasing demand for analytical data from blood samples, sophisticated chemical analyzers have been developed over the past 20 years to perform a multiplicity of physical and chemical tests on specially prepared patients' samples. Regardless of the target analyte, sample volume requirements have been reduced substantially, to 100 uL or less for some tests. Whether the objective is a simple glucose assay, a leukocyte count, or a screening for a particular analyte, the potential risk of specimen contamination and the spread of any infection from the specimen after its collection remains unknown to the health-care worker. In most recent years this factor alone had contributed to the spread of several cases of highly infectious viral diseases such as AIDs and Hepatitis which could have been prevented if the samples were identified and treated accordingly.

There currently exists a need to collect and test biological fluids for the presence of diseases such as cancer or the presence of foreign bodies such as drugs which can be quickly and easily accomplished through visual quantitative testing. A new technology, along with the methodologies for implementation, to fully integrate the steps involved in the collection and processing of blood for diagnostic analysis is needed to: minimize the time required to obtain a clinically relevant answer regarding the patient's health; minimize the health risk associated with handling patients' samples; ensure positive patient identification for the samples and be a user-friendly and transparent to the user. cl Theory and Design of Immunoassays The family of immunoassays works upon the single principal that is the specific recognition of an antigen by an antibody. The specific antigen detection and quantification requires an antibody which recognizes the uniqueness of an antigen. One unique binding site serves as an identifying marker for that protein. Thus detection can be direct where the antigen-specific antibody is purified, labelled and used to bind directly to the antigen or indirect where the antigen-specific antibody is unlabelled and need not be purified. In indirect detection the binding to the antigen is detected by a secondary reagent such as labelled anti-immunoblobulin antibodies or labelled protein A. A variation that uses aspects of both the direct and indirect methods modifies the primary antibody by coupling to it a small chemical group such as biotin and dinitrophenol (DNP) so that the modified primary antibody can then be detected by labelled reagents such as a biotin binding protein or hapten-specific antibodies such as antiDNP antibodies.

Solid-phase Immunoassays

The design of immunoassays for the detection and quantitation of biomolecules in a mixture of cross-reactive molecules can differ from smaller molecules such as hormones and drugs. Antibodies which are immobilized (irreversibly bound) on a membrane are well known in the art and such antibodies are designed to have binding sites which have high affinity for the epitopes of the antigens carried in the saliva and vice versa. Covalent binding of protein to the membrane surface offers permanent binding which is irreversible, so that once a protein like an antibody is bound, it will not be desorbed during an assay. The principle of affinity chromatography requires that a successful separation of a biospecific ligand is available and that it can be chemically immobilized on a chromatographic bed material, the matrix. Numbers of methods well known in the art have been used to couple or immobilize the ligand to a variety of activated resins.

Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G manufactured by Pharmacia, Hydrazide AvidGel Ax manufactured by BioProbe International, and Actigel-ALD manufactured by Sterogene Bioseparation Inc.).

When a definitive antibody for a given antigen is available, it is used to identify the antigen in the sample mixture. Once the antibody combines with the antigen, a means is needed to recognize the complex. This has been accomplished in the past by providing a labelled antibody, such as an enzyme, enzyme link immunosorbent (ELISA)-type assay so that the site is incubated with a chromogenic substrate and a color is developed whose intensity is proportional to the enzyme label present.

Particle-based Diagnostic Tests

Microspheres or uniform particles of many sizes are used in wide variety of modern diagnostic tests and assays. Particle-based diagnostic tests and qualitative/quantitative assays are usually based upon the specific interaction of antigen and antibody. Antigen or antibody can be adsorbed onto submicron sized polystyrene (PS) particles, often called "uniform latex particles". These sensitized particles then act to magnify or amplify the Antigen-Antibody reaction which takes place when a sample containing the target molecule sought is mixed with these appropriately coated particles. In the classic example, a positive test results when uniformly dispersed milky appearing Ab-coated particles in a drop of water on a glass slide react with Ag in a drop of sample (whole blood, serum, urine, etc.) to cause particle agglutination (coagulation or clumping). An improvement in Latex Agglutination Tests (LATs) is the use of dyed particles which provide different contrast (dyed particles observed against a white background). They also permit some tests using samples of whole blood, if dark blue or black particles are used. As an example of the versatility of dyed particles, Wellcome Diagnostics (Dartford, Kent, England) has a Salmonella test which uses antibodies to three different antigen groups bound to three different colored particles (red, blue and green). By comparing the shade of the color of the combined agglutinated particles to a background color, one can decide which of seven combinations of Salmonella groups are present in the sample.

Enzyme Immunofiltration Assays (EIFA)

EIFA utilize microporous membranes as the receptor bearing solid phase and employ filtration as a means to hasten contact with the soluble sample ligand and the signal generating reagents. To prepare these tests, Ab is adsorbed onto PS particles; the particles are caught on a filter and dried. In use: First, a sample is passed through a filter and any Ag is caught by the Ab on the particles. Next, a second Ab-enzyme reacts with it to create an insoluble colored product which is proportional to the amount of Ag caught. The diffusion limitation of the reaction rate seen for conventional solid phase immunoassays is minimized in EIFA. This is due to the flow of reactants through the receptor bearing membrane solid phase and the high ratio of microporous membrane surface area to liquid volume. Thus, EIFA permits rapid tests to be developed which reach completion in minutes. The antigen-antibody reactions in EIFA are visualized directly by immunostaining, in which the signal-generating conjugate yields colored spots at the reaction sites on the membrane. The color intensity of these spots can be quantitiated by reflectance photometry.

Various EIFA methods have been described for the detection of antigens by means of direct binding of sample to the membrane of by employing two antibodies in a sandwich. Detection of antibodies by permutations of this method has also been described. In the sandwich assay described by Valkirs and Barton, rapid flow followed by a short incubation period was used to give a total assay time of 5 minutes. Quantative assays based on EIFA have reproducibility and sensitivity comparable to that of other enzyme-linked immunosorbent assay (ELISA) techniques, the EIFA system can be incorporated in a unit which, besides, the antibody-bearing solid phase, includes an absorbing material for drawing liquid through the membrane and a waste reservoir. Because of their convenience, simplicity, and speed EIFA devices can be used in technically unsophisticated patient environments, i.e., as near patient tests. Various tests (like HCG, "strep"A, and others). using this principle have been made by Hybritech (ICON), Abbot (Testpack), Novo Nordisk A/S (NovoClone Target), and many others. Murex SUDS uses liquid reagents in their tests: mixing Ab-coated particles "Ag (from sample) + second Ab-enzyme conjugate; then pouring the mixture through their filter device to capture the particles which are rinsed with enzyme substrate to form color.

Filter Separation Agglutination Tests (Assays)

Kodak's earliest Surecell test kits used dyed agglutinated particles caught on a filter. Red-dyed particles coated with Ab were incubated with a sample and poured on a filter. Single particles passed through the filter and no color appeared on the surface. If the sample contained the appropriate Ag, the particles agglutinated and the agglutinated clumps were caught on the filter resulting in a red (or pink) positive color test for the Ag. This principle could easily be applied to an assay procedure where the reflected color intensity would correlate with the sample's Ag content. Costar Corp. has proposed a particle agglutination capture ELISA scheme. After reaction with chromogenic substrate, soluble substrate is measured in a spectrophotometer (microplate reader).

Improved Dyes and Latex

Small microspheres with bright, photostable fluorescent or colored dyes have opened up new opportunities for sensitive diagnostic tests. Fluoroescent latex is inexpensive and widely applicable to qualitative and quantitative immunodiagnostics. The use of fluorescent latex particles should be applicable to most, if not all of the major latex-based diagnostic test systems presently in use, including latex agglutination tests (LAT), filter separation tests (in which agglutinated particles are trapped on a filter), particle capture ELISA methods and two-particle sandwich techniques. The increased signal available from fluorescence offers the option of quantitative, as well as qualitative results, with potential sensitivity increases of over 1000-fold, compared to colorimetric methods.

Several areas for latex particles in ultra-sensitive diagnostic tests are outlined as follows:
- Latex Agglutination Tests (LAT)/Latex ImmunoAssay (LIA)
- Agglutination/Capture Tests & Assays (Dyed Particles)
- Particle Capture ELISA Tests & Assays
- Dyed-Particle Sandwich Tests & Assays
- SPRIA/SPEIA, DNA Probes (solid/liquid separation via centrifuge or magnet).

DESCRIPTION OF THE PRIOR ART

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,77,739; 3,881,465; 4,042,337; 4,084,937; 4,244,920; 4,492,258; and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of urine. U.S. Pat. No. 4,573,983 is directed to a liquid collection system having an antiseptic member on the discharge section which uses a filter of air and bacteria impervious material to filter urine.

The present inventor presently has a number of U.S. Patents issued to him directed toward testing devices for biological fluids. U.S. Pat. No. 5,022,411 discloses an apparatus for testing biological molecular indicators in urine comprising a tubular container with a plunger assembly and associated testing assembly. Urine collected in the tubular container is mixed with labelled antibodies and is caused by the plunger assembly to flow against a testing surface provided with immobilized antibodies which capture antigens complexed with labelled antibodies. The enzymes of the labelled antibodies are colored by a reactant solution to indicate the presence or absence of specific antigens in the tested urine.

U.S. Pat. No. 5,016,644 discloses a method for testing for biological molecular indicators in urine. Urine is transported through a sample container under pressure to flow through the sample container so that antigens in the urine are collected and bound on antibodies immobilized on the beads to form antigen-antibody complex. The beads are washed to remove cell debris and a specific prelabelled antibody solution is passed through the sample container with the prelabelled antibodies attaching to a receptor site on the captured antigen to form an antibody-antigen-prelabelled antibody sandwich complex. This sandwich complex is washed to remove cell debris and charged molecules and mixed with a color reagent solution which reacts with the prelabelled antibody to produce a color indicating the presence of a specific cancer antigen.

U.S. Pat. No. 5,003,988 discloses an apparatus for collecting and testing multiple biological markers comprising a tubular compartmentalized container holding covalently bound antigen beads contained in separated compartments. The biological fluid is collected in the tubular container and is forced to flow through the separated compartments of the compartmentalized container so that predetermined ligands become attached to the bead ligand to obtain a plurality of biological markers.

U.S. Pat. No. 4,961,432 discloses an apparatus for collecting biological fluids and handling the same into a sample for testing comprising a tubular container having open ends, one of which is removably secured to a collection storage unit. A shuttle assembly constructed of a cylindrical hollow piston defining a chamber, a top cover covering one end of said piston and a second cover with an aperture and a connector covering the second end of the piston is slidably mounted in the tubular container. An "O" ring is mounted on the exterior surface of the piston to form a fluid tight seal between the "O" ring and the interior surface of the tubular container with the connector being removably secured to a resin/sample container so that movement of the piston in the tubular container carries the resin/sample container into the collection storage unit and forces fluid collected in the tubular container to flow through the resin/sample container.

U.S. Pat. No. 4,960,130 discloses an apparatus for collecting biological fluids and handling the same into a sample for testing comprising a tubular container having open ends, one of which is removably secured to a collection storage unit. A shuttle assembly constructed of a cylindrical hollow piston defining a chamber, a top cover covering one end of said piston and a second cover with an aperture and a connector covering the second end of the piston is slidably mounted in the tubular container. An "O" ring is mounted on the exterior surface of the piston to form a fluid tight seal between the "O" ring and the interior surface of the tubular container with the connector being removably secured to a resin/sample container so that movement of the piston in the tubular container carries the resin/sample container into the collection storage unit and forces fluid collected in the tubular container to flow through the resin/sample container.

U.S. Pat. No. 4,953,561 discloses an apparatus for testing biological molecular indicators in urine comprising a tubular container, and a sample container holding beads with immobilized ligands. Urine is transported through the tubular container under pressure to flow through the sample container which screens off the antibodies so that antigens carried by the urine fluid are collected and concentrated on the beads.

The present invention is also an apparatus which allows the easy visual identification of markers carried in biological fluids.

BRIEF SUMMARY OF THE INVENTION

The invention is directed toward a biological fluid collection and testing device, preferably a blood testing device. This device is in the form of a vial having an interior container, such as a blood test container rotatably seated in the vial with a side of the container being provided with a capillary marker assembly for capturing a ligand, or member of a biospecific complex pair, such as a specific antibody or, preferably, specific antigen allowing visual identification of the specific antigen. The fluid, preferably blood is added to the vial through a sealed cap. In the interior container, the fluid engages a flow through filter membrane in the bottom of the container having <5 micron pore size, which membrane is seated over a reaction well in the vial. The filter membrane provides the surface upon which red blood cells engage but cannot pass allowing blood serum which has a pH of 7.2 to pass through it into the well of the vial filling the well. When present, as for example an analyte, the first ligand or member of the biospecific complex pair, typically serum antigen reacts with a labelled second member of the biospecific complex pair, typically a lyophilized labelled antibody, housed in the capture well adjacent the treatment container to form a biospecific complex pair, such as an antigen-antibody complex. The vial is rotated to a first position, for example through an angle of 90°, to disconnect the serum in the reaction well from the rest of the blood in the interior blood container to prevent any back diffusion of the labelled antibody to the blood container. After a brief incubation time, the vial is then rotated to a second position, for example through a total angle from the initial positions of the vial end interior container, of 180° until the capillary marker assembly is positioned over the filled well. This relationship between the well and the capillary marker assembly causes the serum to move along a membrane strip in the capillary marker assembly. In the typical situation where the analyte is the first member of the biospecific complex pair, such as an antigen, if there is an absence of the antigen in the specimen (serum) sample, the labelled second member of the biospecific complex pair, such as labelled antibody, will remain unoccupied and seek the binding site of antigen coated polymer particles present on membrane a a control zone of the capillary assembly. A complexed antigen/labelled antibody from the well as carried by the capillary action of the serum into the capillary marker assembly does not react to polymer particles having immobilized antigens in the control zone. Rather the complexed antigen/labelled antibody is transported to a second test zone on the membrane. This second zone is provided with polymer particles having second capture antibodies which capture the complexed antigen/labelled antibody which is visible through the clear wall of the vial to produce a visual color. The amount of the second capture antibodies (binding sites) in the test zone is predetermined so that the number of the filled sites with the complex antigen/labelled antibody can be quantified by the marks on the capillary meter assembly. The test result indicating presence or absence of an analyte such as, a cancer or drug, etc. is thus visualized by a color or lack of color. While collodial gold substrate is preferred over other dyed particles or microsomes, a chromogenic substrate provides an alternative sensitive detection method for an enzyme conjugate.

It is thus an object of the invention, particularly where members of biospecific complex pairs, or ligands, such as antigens and antibodies are being removed from body fluids for testing to detect and visually quantitate a specific member of a biospecific complex pair, such as an antigen in the body fluid samples. Previously such testing has been accomplished using several independant steps involving sample collection, aliquoting, and transporting the sample to test devices which have been discussed in the background of the invention.

In the accompanying drawings, there is shown an illustrative embodiment of the invention from which these and other of objectives, novel features and advantages will be readily apparent.

BRIEF DESCRIPTION OF THE DRAWINGS

FIG. 6 A is a partial cross sectional view showing the tip member of the apparatus of FIG. 6 prior to rotation of the components and travel of the antigens through the filter into the well;

FIG. 7 is a schematic representation of the apparatus in FIG. 6 showing rotation of the relative components of the apparatus to assume the configuration of FIG. 8;

FIG. 7 A is a partial cross sectional view showing the tip member of the apparatus in FIG. 6 after it has been partially rotated (90° rotation) as shown in FIG. 7;

FIG. 8 is a cross sectional view of the apparatus in FIG. 6 after a 180° rotation showing seating of the capillary tube assembly over the serum separation well;

FIG. 8 A is a partial cross sectional view showing the tip member of the apparatus of FIG. 8 after it has been fully rotated to align the well with the capillary tube foot;

DETAILED DESCRIPTION OF THE INVENTION

Figure 1:
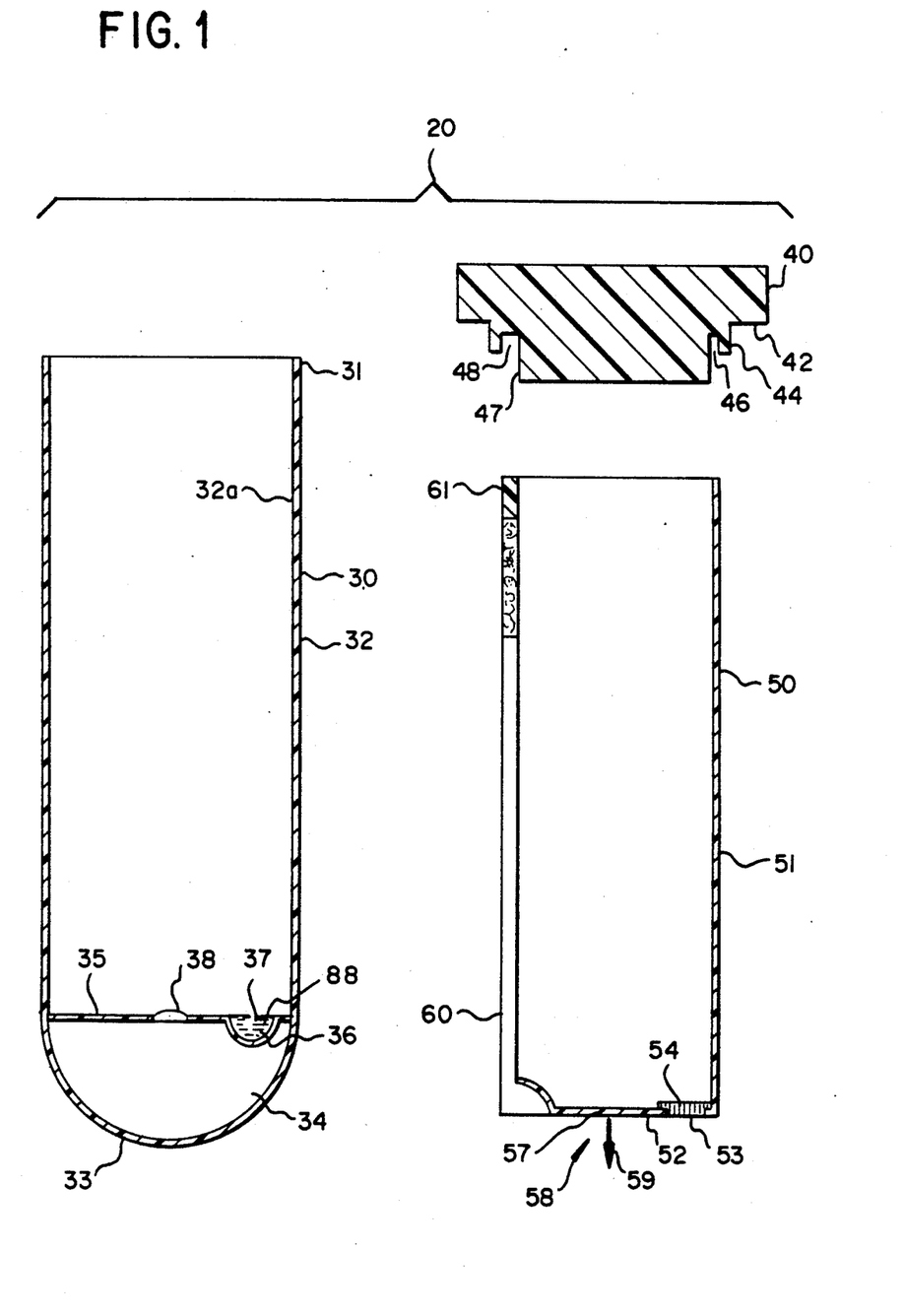
FIG. 1 is an exploded cross sectional view of the fluid testing apparatus of the present invention.

The best mode and preferred embodiment invention is shown in FIGS. 1-13. In the invention, a fluid collection and testing apparatus 20 is constructed of a closed end housing 30 formed by tube wall 32 and a rounded distal tip 33. While the present invention is primarily directed toward the testing of blood it is appreciated that other biological fluids such as urine can be used in this invention. A tip member 34 having a top planar surface 35 is seated within the closed rounded distal tip portion 33 and defines a collection well and reaction chamber 36. The well 36 contains or is provided with mouse anti-antigen antibody 88 labelled with colored latex 89 which will mix with the filtered blood serum entering the well as will be later described. If desired the well can be covered with a porous membrane 37 as shown in FIG. 1 to prevent spillage of the colored latex from the collection well. The tip member 34 is also provided with a female receptacle 38 adapted to receive a male member 58 having a shaft 57 and an arrowhead shaped tip 59 extending from a fluid container 50 which is snap fitted in receptacle 38 holding the container 50 in the tip member 34 while allowing rotation of the container in two phases, first 90° rotation to disconnect the reaction chamber from the blood container after filling the reaction chamber with the serum and to allow for a brief incubation period of the reactants in this chamber, second a 180° rotation to align the reaction chamber with the capillary meter assembly. The fluid container 50 comprises an open ended tubular wall 51 with a flat end wall 52. The end wall 52 defines a flow aperture 53 in which is seated a filter 54 for filtering the fluids. The filter 54 preferably has a <5 micron pore size to allow easy flow of blood serum. The end wall 52 also defines the pivot assembly 58 comprising shaft 57 which extends outward from end wall 52 and a locking tip 59 which is preferably arrowhead shaped to fit in receptacle 38 holding container 50 in the housing 30. A capillary meter assembly 60 is secured to the side of the fluid container wall 51 opposite the filter 54.

Figure 9:
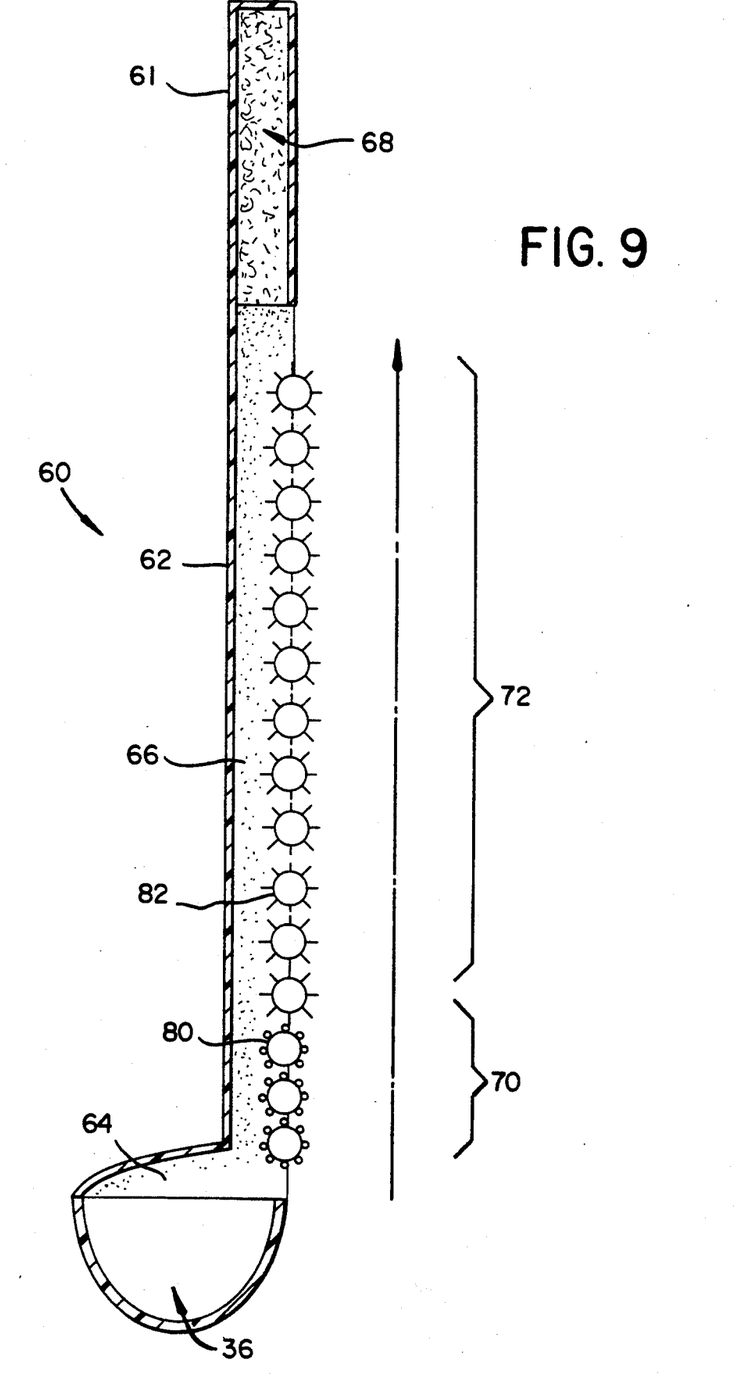
FIG. 9 is an enlarged cross sectional view of the capillary tube seated over the filtered well with schematic representation of antigen and antibody covered particles embedded in a capillary membrane in control and test zones respectively.

The capillary meter assembly 60 is constructed with a capillary tube or conduit 62 and a well reaction cover flange or foot 64 at one end which fits over the well 36. The tube holds absorbent material 68 in the end portion opposite the foot 64. The absorbent material abuts a membrane strip member 66 which extends into the foot area. This membrane strip aids in the capillary action so that the fluid serum will move upward from the well 36 through the foot along the membrane strip 66 into the absorbent material 68. The membrane strip 66 is provided with a control zone 70 as shown in FIG. 9. The control zone 70 contains antigen coated polystyrene particles 80 trapped in the membrane 66. The membrane 66 is also provided with a test zone 72 again as shown in FIG. 9 which has anti-antigen antibody coated polystyrene particles 82 trapped in the membrane 66.

The preferred membrane used in the invention is Gelman Supor membrane. Supor membrane is a low protein binding polysulfone membrane with a hydrophilic surface, superior flow rate, and particle retention. Gelman Supor Membranes provide a smooth surface, brilliant whiteness and opaqueness to enhance signal contrast in diagnostic tests. Low extractables reduce sample contamination, uniform porosity ensures final product consistency, and no external wetting agent which prevents the introduction of unwanted extractables. These unique performance characteristics of Supor make it ideal for the inventive device. While a solid phase membrane 14 is a preferred synthetic membrane of low protein binding with antigen or antibody coated particles entrapped on its surface, other membranes with high protein binding can be used to immobilize the antigen or the antibody directly on their surface. The use of membranes as the solid phase eliminates handling, allow the product configuration to be cut in the desired shape or format for placement on a base, and provides faster kinetics and increased protein binding. Protein binding to solid plastic substrates has been found to be a non-stoichiometric process and varies greatly by the type of plastic used. Binding is not specific and generally occurs through electrostatic and hydrophobic interractions between plastic and proteins. Membrane substrates overcome many of the problems inherent in solid phase immunoassays as they combine the qualities of a solid substrate with a range of expanded capabilities and, due to their porosity and consequential large surface area, have a high protein binding capacity. Protein binding capacity is increased by using smaller pore sized membranes whose total binding surface increases for an equivalent frontal surface. Membranes which can be used in the present invention in addition to the noted latex entrapment membranes can be constructed of nitrocellulose, nylon, cellulose or IAM produced by Millipore, Inc. The choice of adsorbing matrix depends on the physical properties such as sensitivity, binding capacity, stability or bound molecules and compatibility with the assay system. Membranes, such as nylon and cellulose, can be modified to create surface sites for covalent binding or proteins. Nitrocellulose is one of the most commonly used membranes due to its high affinity for proteins and cellular macromolecules. In IAM, polyvinylidenedifluoride (PVDF), the base polymer of IAM is hydrophobic and binds proteins. IAM permits a high degree of control over the extent of protein binding and the user can reproducably immobilize nanogram to microgram quantities of protein on the surface to suit various assay requirements. Binding the protein to IAM surfaces occurs primarily through the epsilon amino group of lysine, which contrasts the binding proteins to nitrocellulose, nylon or plastic where the bonding is ionic or hydrophobic.

Another type of membrane which can be used in the invention which has previously been noted is nitrocellulose which provides an excellent matrix for blotting proteins and nucleic acids. The nitrocellulose may be cut into whatever shape is required. Pure nitrocellulosse adsorbs proteins, nucleic acids and other cellular antigens. These adsorbed substances often retain antigen-antibody binding activity and can be visualized using ultrasensitive, enzyme amplified immunostaining methods so that a chromogenic stain marks the location of the adsorbed materials. This approach uses a technique called Dot ELISA, (which also can be utilized with the Nylon, IAM, plastic membranes) whereby nanogram amount of protein are directly applied to nitrocellulose. One important advantage of Dot ELISA is the ability to perform multiple enzyme immunoassays in a single test procedure using as little as one microliter of antigen or capture antibody solution. Nanogram amounts of capture antibodies dotted onto a single membrane can be used to screen simultaneously for a variety of antigens. In a Dot ELISA procedure the reactant is diluted in coating solution and dotted onto the damp membrane. While the optimal concentration will vary from reactant to reactant, for complex antigens 0.1–1.0 mg/ml is suitable. Following membrane blotting excess binding sites are blocked by thoroughly soaking both sides of the membrane in Diluent/Blocking Solution. Any of a variety of reservoirs can be used. The Diluent/Blocking Solution contains 1% bovine serum albumin (BSA) in phosphate buffered saline which protects adsorbed protein from surface denaturation. Following the blocking step, membranes can be stored dry at refrigeration temperatures for several months without loss of activity. The adsorption of an antigen or capture antibody onto the Nitracellulose membrane can be accomplished by Antigen Detection ELISA, Indirect Antibody ELISA which is capable of detecting either antibody or antigen, depending on which is defined as the unknown or Antibody Sandwich ELISA which is accomplished by adsorption of an antigen or capture antibody, washing each reagent of any free or unattached reactant and adding another reagent to build, step by step, a molecular sandwich on the membrane surface which is completed by the addition of an enzyme-antibody conjugate. The construction of such membrane surfaces is clearly shown by a bulletin of Kirkegaard & Perry Laboratories, Inc. 1985 entitled ELISAmate (TM) Enzymme Immunoassay Test System for Detection of Antigens or Antibodies on Membranes which is incorporated in this application by reference.

Figures 2, 3:
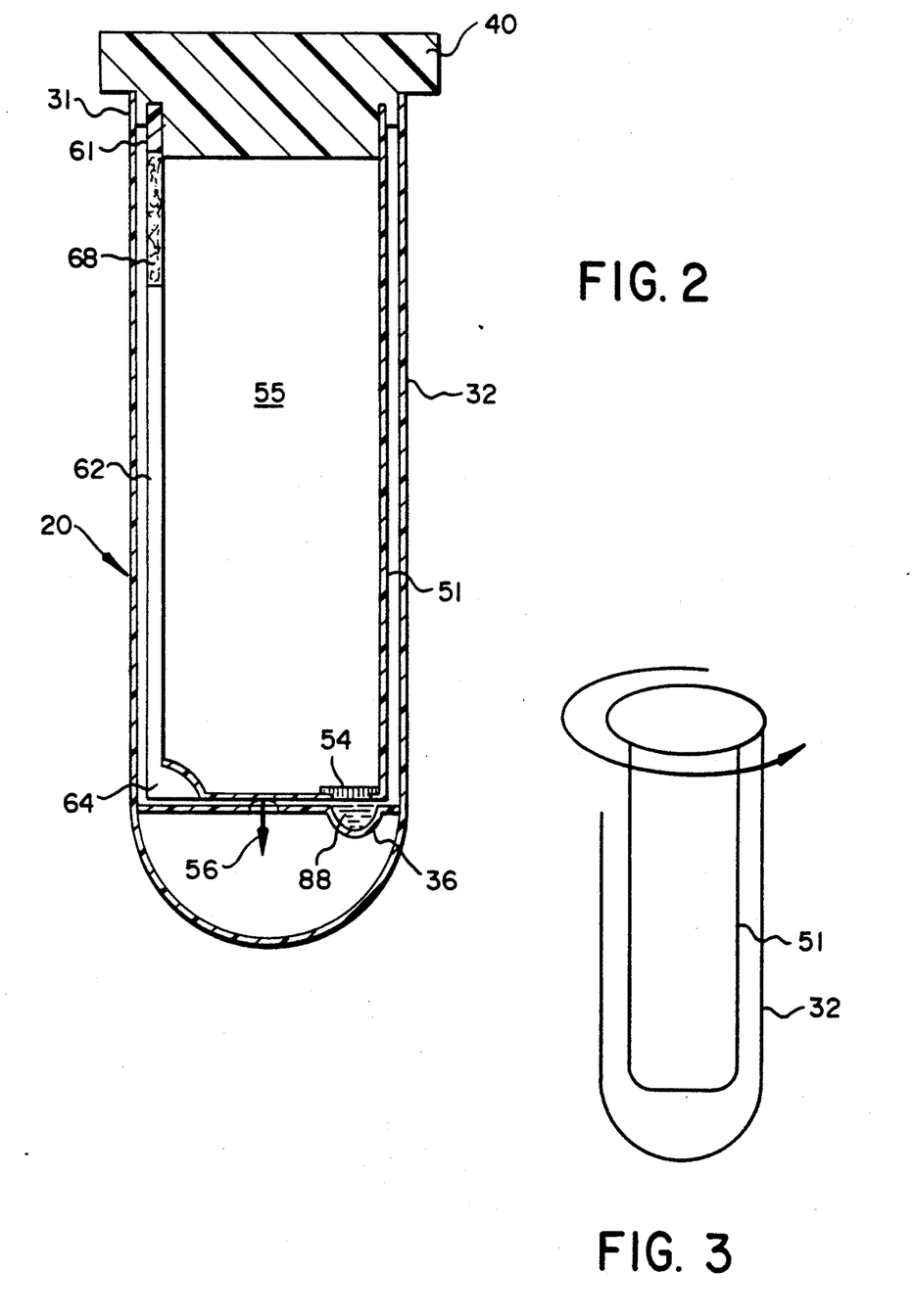
FIG. 2 is a cross sectional view of the assembled fluid testing apparatus shown in FIG. 1.
FIG. 3 is a schematic diagram of the apparatus of FIG. 2 rotated to assume the changed component position shown in FIG. 4.
Figures 4, 6:
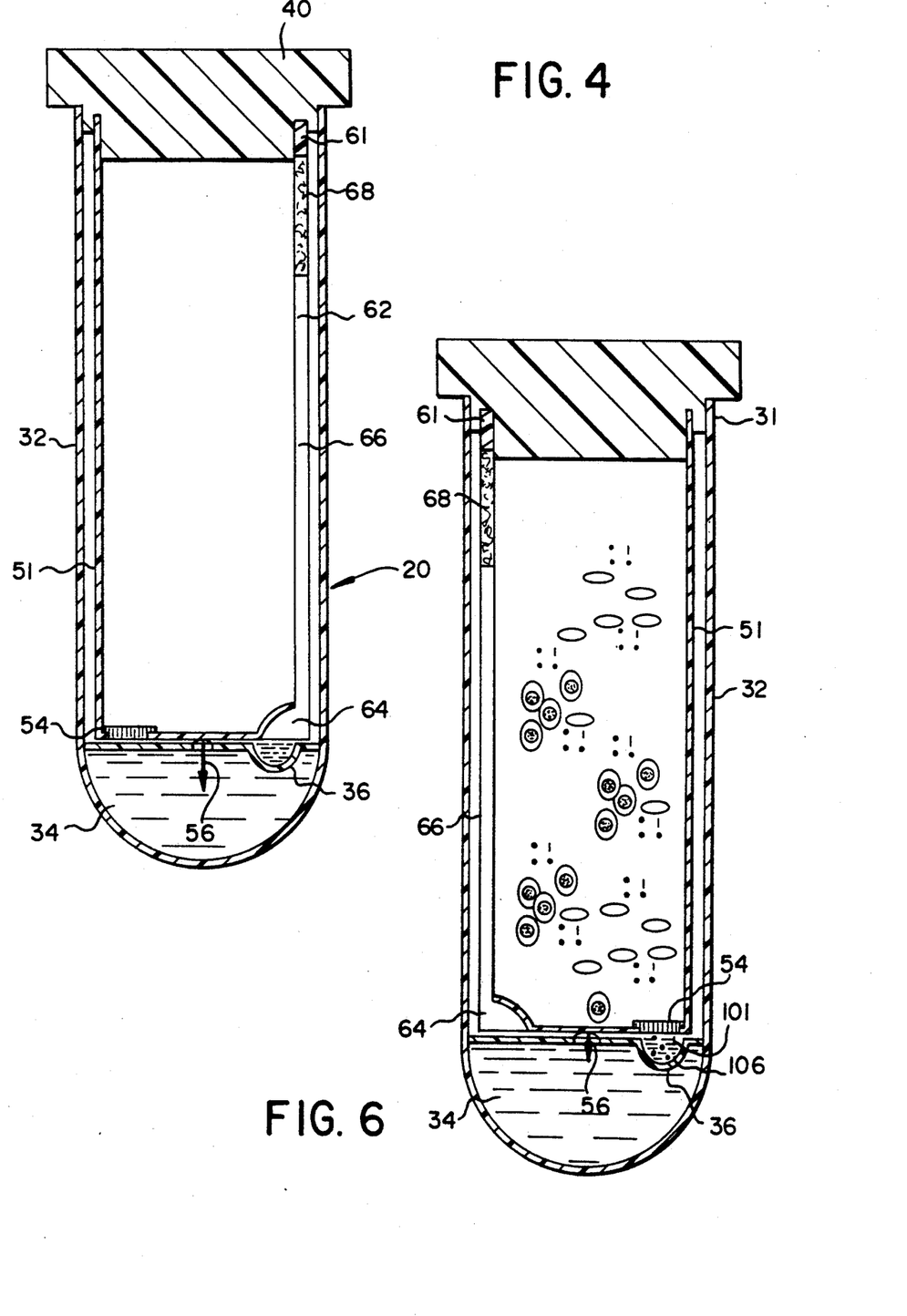
FIG. 4 is a cross sectional view of the apparatus shown in FIG. 2 after the same has been rotated as shown by a schematic FIG. 3.
FIG. 6 is a cross sectional view of the apparatus shown in FIG. 5 after it has been removed from the collection needle and shows volumetric serum separation into the filtered well.
Figure 5:
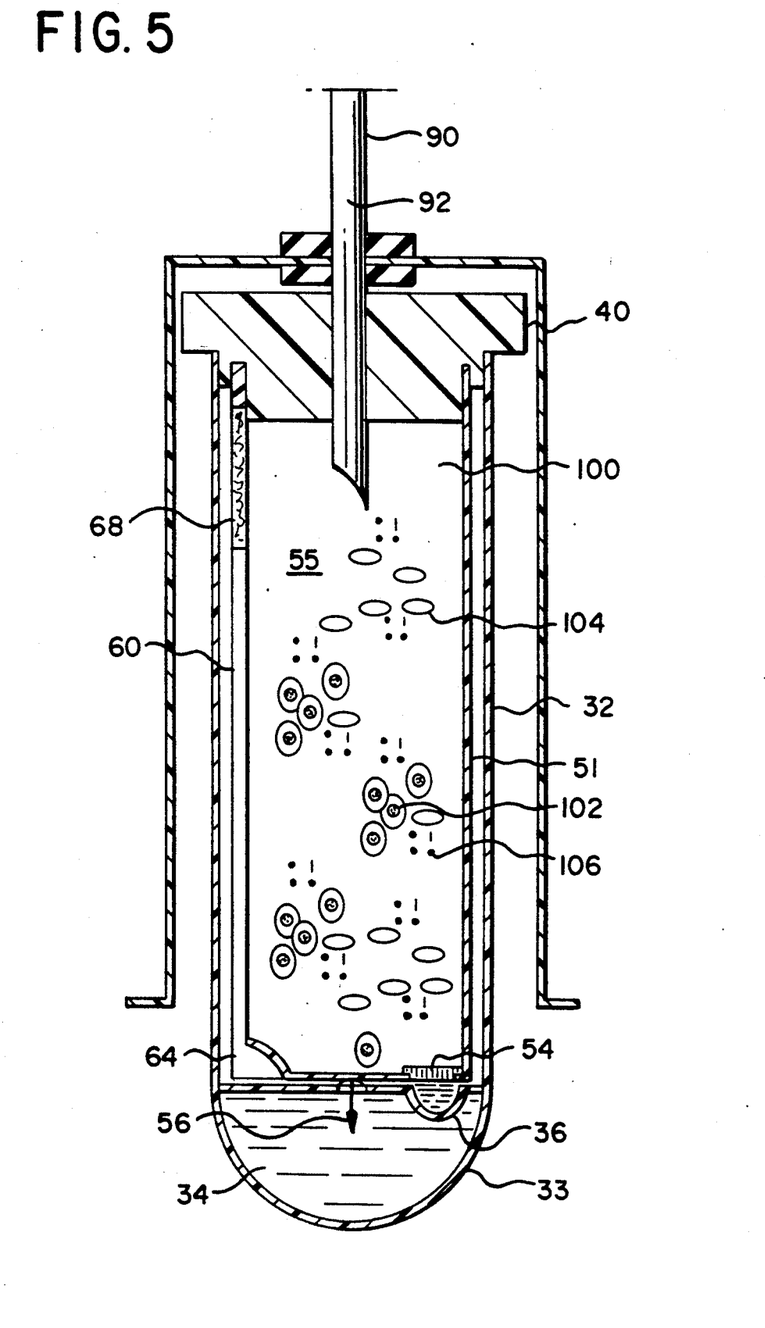
FIG. 5 is a cross sectional view of the inventive testing apparatus showing blood being withdrawn through a needle lumen into the collection container of the invention.
Figures 6A, 7, 7A, 8, 8A:
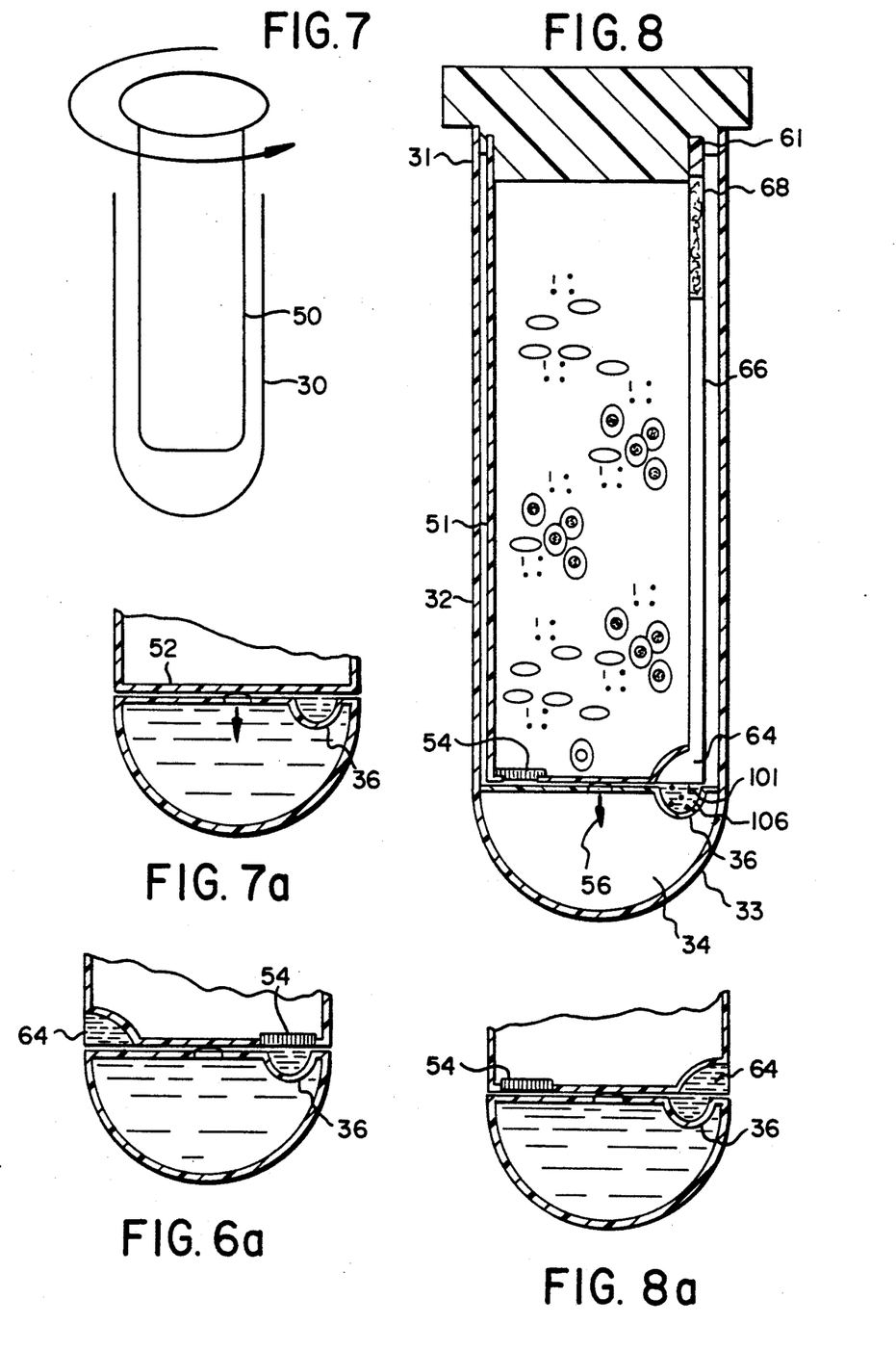

An elastomeric cap member 40 is provided for the invention. The cap member 40 has a shoulder 44 and lip 42, the shoulder's exterior surface being designed to snugly fit within the inner surface 32a of tube 32 and the lip 42 is seated against the top surface 31 of tube 32. The shoulder 44 is provided with an annular channel 46 which holds the open end of the fluid container wall 51 up against the stopper wall 47. The channel 46 is provided with a widened area 48 which receives the top portion 61 of the capillary meter assembly 60 to hold the fluid container 50 in a snug secured position in the cap member allowing the fluid container 50 to be rotated within the tube housing 50 as is shown in FIG. 3. FIG. 5 shows the insertion of a needle 90 with lumen 92 through the elastomeric cap member 40 into chamber 55 of fluid container 50. Blood or other fluid is introduced from a source through the needle 90 into chamber 55 as shown in FIG. 5. The blood 100 contains serum 101, cells 102, cell debris 104 and antigen 106. The testing apparatus 20 is removed from the needle 90 and connected blood or fluid source and the elastomeric cap member seals from the needle puncture. It should be noted at this time that the filter 54 of the fluid container is positioned directly over the well and reaction chamber 36 of tip member 34 so that there is a volumetric serum separation of the blood, in that serum from the blood passes through the filter 54 into the well 36. The serum mixes with lyophilized mouse anti antigen antibody 88 labelled with colored latex 89 previously added to the reaction chamber of the well 36. The housing 30 is then rotated around the container 50 on pivot assembly 38 in two steps, first 90° rotation to disconnect the reaction chamber from the fluid container and to allow for a brief incubation period of the reactants in the reaction chamber, second a 180° rotation until the well 36 with the serum composite is positioned adjacent to the capillary meter assembly 60 with the cover or foot 64 of the assembly covering the reaction chamber of the well 36. Capillary action of the fluid in the well containing the mouse anti-antigen antibody labelled colored latex then occurs. When there is no complexing of the labelled antibodies, the ligands travel through the capillary tube as shown in FIG. 10.

Figures 10, 11:
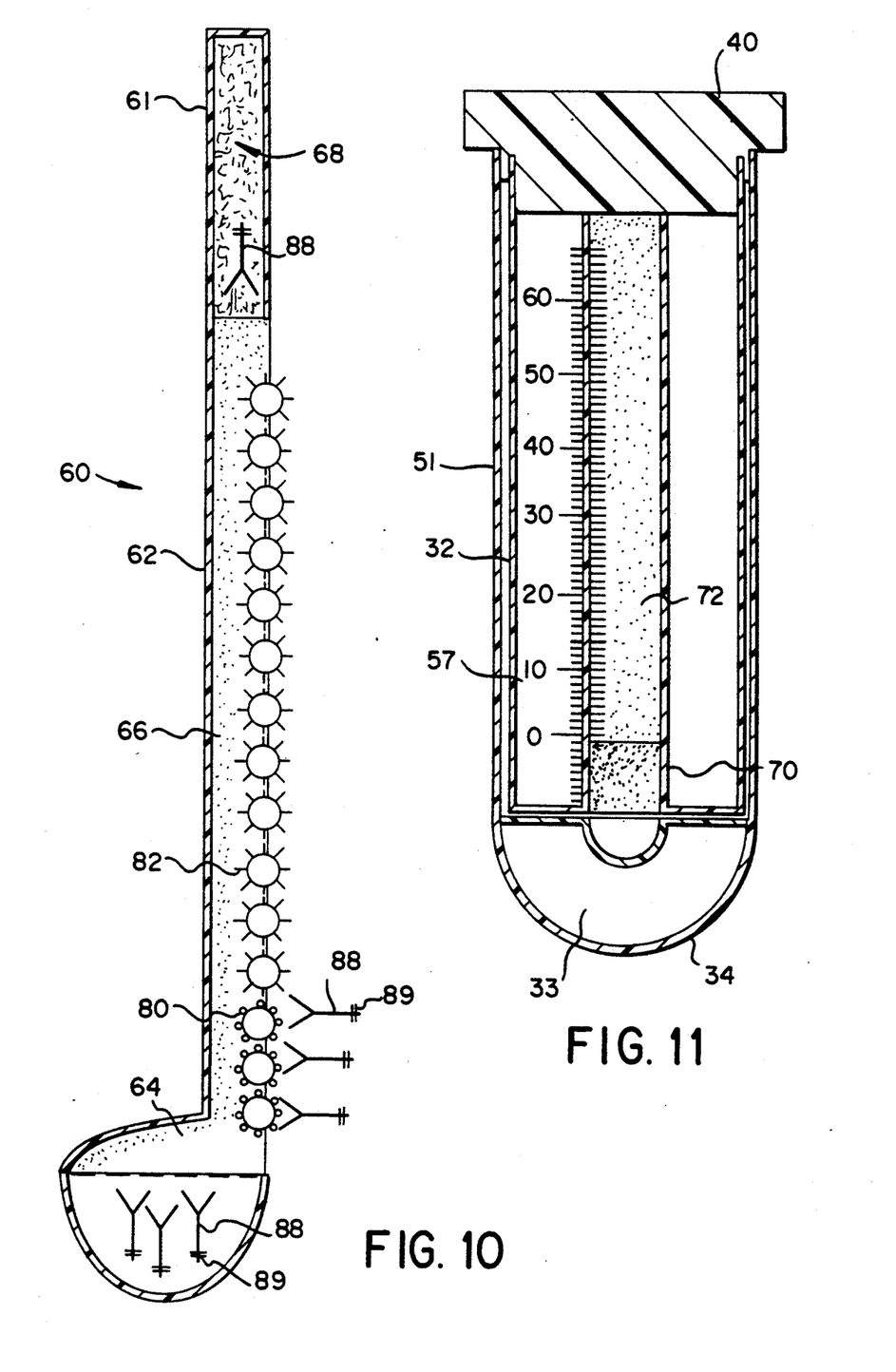
FIG. 10 is a cross sectional view of the embodiment shown in FIG. 9 in which labelled antibodies in the filtration well have migrated via capillary action up the capillary tube and attached to the ligand covered particles of a membrane in the control zone.
FIG. 11 is a front elevational view of the capillary tube showing the presence of specific labelled antibodies on the membrane in the control zone.

As shown in FIG. 11 the result of this test is shown by the coloration present against the marking indicia 57 formed on the outside surface of the fluid container tube 51, to indicate the amount of filled vs. unfilled sites of the predetermined binding sites in the test zone.

Generally, the color produced is proportional to the amount of unknown or analyte present in the sample, providing the unknown is the limiting component of the system. The BCIP,NBT Phosphates Substrate System generates a dark purple stain on membrane sites bearing phosphatose. Alkaline phosphatase catalyze the dephosphorylation of 5-bromo-4-chloro-3 indolyl phosphate which initiates a reaction cascade resulting in intense color formation. Binding of an antibody can be detected by a variety of reagent systems as is the case for antigen bound to the antibodies of the membrane. For instance, I-labelled antimouse immunoglobulin or I-labelled protein A may be used. Antimouse immunoglobulin conjugated directly to alkaline phosphatase or to peroxidase may be used, together with appropriate chromogenic substrates. The biotin-avidin peroxidase system can be used together with appropriate chromogenic substrates. The biotin avidin peroxidase system (for example, the Vectastain ABC system supplied by Vector Laboratories) is particularly sensitive.

Figures 12, 13:
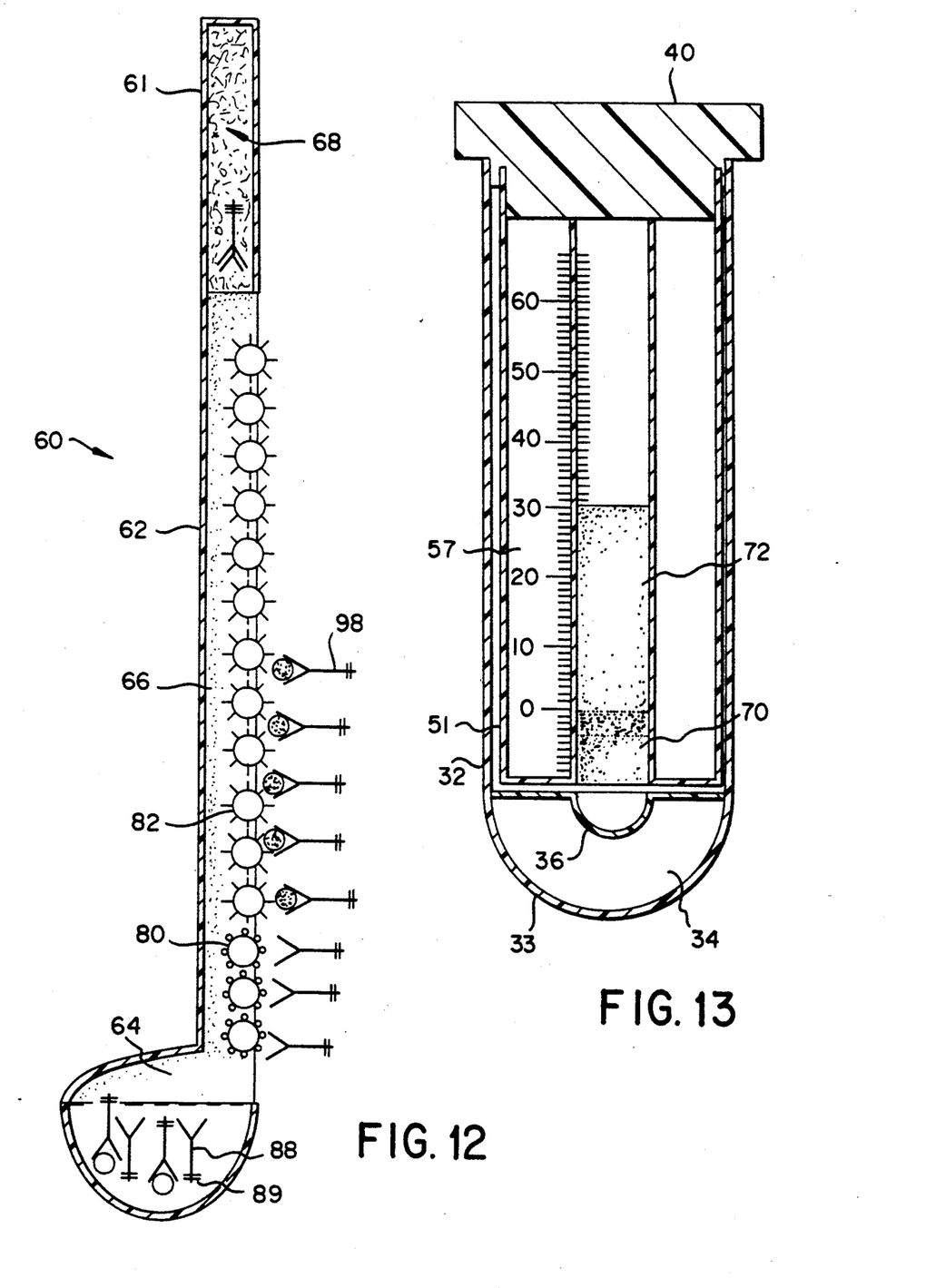
FIG. 12 is a schematic cross sectional view of the capillary tube of FIG. 9 in which complexed antigen and labelled antibodies in the filtration well have migrated via capillary action up the capillary tube and attached to the ligand covered particles on the membrane in the test zone.
FIG. 13 is a front elevational view of the capillary tube showing the presence of specific complexed antigen/labelled antibodies.

In FIG. 12 the capillary action is shown where a complexed antigen/antibody 98 with labelled colored latex is captured by the particles 82 in the test zone 72 to indicate a positive test result. Visual representation of such testing is shown in FIG. 13.

Figures 14, 15:
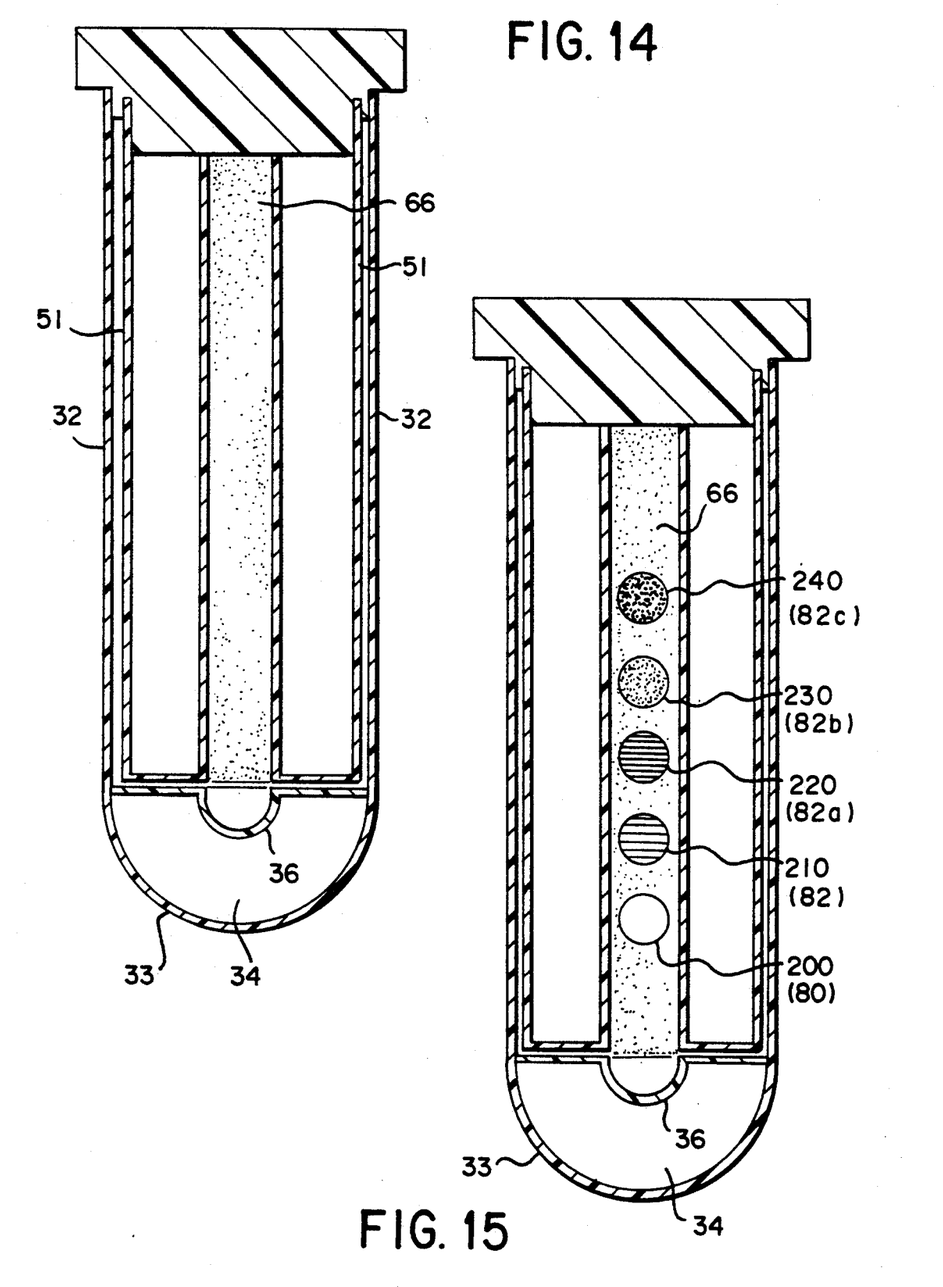
FIG. 14 is an alternate embodiment of the present invention showing a cross sectional view of an apparatus for multiple ligand tests.
FIG. 15 is the invention shown in FIG. 14 in which the presence or absence of multiple ligands are visually indicated on indicator areas of the test membrane of the apparatus.

Another embodiment of the invention is shown in FIGS. 14 and 15. In this embodiment there is a control zone 200 corresponding to zone 70 and particles 80 and multiple tests zones 210-240 corresponding to zone 72; each of which is provided with specific test spots or areas, such as specific anti antigen coated polystyrene particle areas 82, 82a, 82b and 82c for different analytes such as antigens representing cancers or other diseases carried by the blood or other fluids for easy recognition through the glass of the fluid container. It is understood that a wide variety of permutations of the antigen/antibody coated/uncoated particles as well as prelabelled antibodies can be used in the inventive device to produce similar results as previously eluded to in the prior art.

The aforementioned inventive device and method provides the following features and advantages: First, the blood sample remains in the blood-collection container during all the processing and separation steps required by the detection device. Such containment automatically ensures positive patient identification and eliminates all peripheral equipment associated with manual aspiration and sample splitting. Also, preventing the external exposure of the sample to the environment minimizes health hazards. Furthermore, because there is no manual manipulation of the samples, processing time is minimized, and numerous other possible sources of operator error are virtually eliminated.

Second, the processes of cell separation and plasma transfer to aliquoating chamber takes place within this blood collection and processing container, without operator intervention. The volume of the serum collected is strictly defined by the aliquoting chamber which in turn will allow a quantitative measurement of the analyte in the serum.

In the foregoing description, the invention has been described with reference to a particular preferred embodiment, although it is to be understood that specific details shown are merely illustrative, and the invention may be carried out in other ways without departing from the true spirit and scope of the following claims:

What I claim is:

1. A fluid collection and testing apparatus comprising a housing, a well positioned in said housing, a container rotatably mounted to said housing adjacent said well, said container being provided with fluid flow means for fluid communication with said well, a filter mounted in said fluid flow means to filter fluid passing into said well and a capillary ligand test assembly secured to said container.

2. A fluid collection and testing apparatus as claimed in claim 1 wherein said capillary test assembly comprises a capillary tube a membrane mounted in said capillary tube and an absorbent material mounted in said capillary tube, said membrane being provided with designated ligand capture means with predetermined number of binding sites to capture specific predetermined ligands.

3. A fluid collection and testing apparatus as claimed in claim 2 wherein said predetermined ligands are complexed antigen/antibodies labelled with a latex label.

4. A fluid collection and testing apparatus as claimed in claim 2 wherein said capillary tube is provided with marking means to indicate the number of filled versus unfilled binding sites in the test zone.

5. A fluid collection and testing apparatus as claimed in claim 2 wherein said membrane is a membrane strip divided into a testing zone and a control zone.

6. A fluid collection and testing apparatus as claimed in claim 5 wherein said testing zone of said membrane strip contains anti-antigen antibody coated polymeric particles trapped in the membrane and said control zone contains antigen and/or goat anti-mouse antibody coated polymeric particles trapped in the membrane.

7. A fluid collection and testing apparatus as claimed in claim 5, wherein said testing zone of said membrane strip contains polymeric particles coated with at least one antiantigen antibody said coated particles being immobilized in said membrane.

8. A fluid collection and testing apparatus as claimed in claim 5, wherein said control zone contains polymeric particles coated with at least one antigen, said particles being immobilized in said membrane.

9. A fluid collection and testing apparatus as claimed in claim 6, wherein said polymeric particles are polystyrene particles.

10. A fluid collection and testing apparatus as claimed in claim 1 wherein said container housing is provided with marking indicia.

11. A fluid collection and testing apparatus as claimed in claim 1 wherein said capillary testing assembly comprises a tube with a foot adapted to cover said well, absorbent material mounted in the opposite end of said tube away from said foot, membrane a mounted in said tube adjacent said absorbent member and extending into said foot, said membrane comprising a membrane strip with antibodies mounted thereto selected to capture specific predetermined ligands.

12. A fluid collection and testing apparatus as claimed in claim 11 wherein said antibodies comprise a plurality of antibody coated polymeric particles embedded in said membrane strip, said antibody coated polymeric particles being specifically selected to capture designated antigen and arranged in separate zones on said membrane so that different antigens will be captured in said different zones.

13. A fluid collection and testing apparatus as claimed in claim 12 wherein said antibody coated polymeric particles are: anti-antigen coated polystyrene particles trapped in the membrane.

14. A fluid collection and testing apparatus as claimed in claim 12 wherein said antibody coated polymeric particles are: goat anti-mouse antibody coated polymeric particles trapped in the membrane.

15. A fluid collection and testing apparatus as claimed in claim 1 wherein said housing has an end member including said well and a pivot for said container.

16. a fluid collection and testing apparatus as claimed in claim 15 wherein said pivot is a receptacle adapted to receive locking means of said container comprising a shaft and head member.

17. A fluid collection and testing apparatus as claimed in claim 1 wherein said well contains anti-antigen antibody labelled with colored latex.

18. A fluid collection and testing apparatus as claimed in claim 1 including a cap mounted to said housing and said container.

19. A fluid collection and testing apparatus as claimed in claim 18 wherein said cap has a shoulder with an annular groove defined therein to receive and hold the open end of said container with a section of said annular groove being widened to receive and hold one end of said capillary ligand test assembly.

20. A fluid testing apparatus comprising a housing, a well located in said housing, a container rotatably mounted to said housing and positioned adjacent said well, a cap mounted to said housing and said container, said container comprising a container housing with fluid flow means allowing fluid communication with said well, a filter mounted in said fluid flow means to filter fluid passing into said well and a capillary ligand test assembly secured to said container housing; said capillary test assembly comprising a capillary tube, a membrane mounted in said capillary tube and absorbent material mounted in said capillary tube, said membrane comprising a membrane strip divided into a testing zone and a control zone provided with designated ligand capture means to capture specific predetermined ligands.

21. A fluid testing apparatus as claimed in claim 20 including a device to introduce biological fluid into the container at superatmospheric pressure.

22. A fluid testing apparats as claimed in claim 21 wherein said introduction a device is an injection apparatus.

23. A fluid testing apparatus as claimed n claim 22 wherein said injection apparatus is a syringe.

24. A fluid testing apparatus as claimed in claim 20 including a device to introduce biological fluid into the container at subatmospheric pressure.

25. A fluid testing apparatus as claimed in claim 24 wherein said introduction a device is a vacuum apparatus.

26. A fluid testing apparatus comprising a housing, a well positioned in said housing, a container rotatably mounted in said housing and positioned over said well, a cap mounted to said housing and said container, said container being in fluid communication with said well, a filter connected to said container into said well and a capillary ligand testing assembly secured to said container housing, said capillary testing assembly comprising a conduit member with a foot adapted to cover said well, an absorbent material mounted in said conduit member away from said foot, a membrane mounted in said conduit member adjacent said absorbent member and extending to said foot, said membrane arranged as a strip divided into a testing zone and a control zone, said testing zone of said membrane strip including antibodies secured to said membrane strip.

27. A fluid testing apparatus as claimed in claim 26 wherein said antibodies comprise a plurality of embedded antibody coated polymeric particles, said antibodies being specifically selected to capture designated antigen in separate zones on said membrane so that different antigen will be captured in said different zones.

28. A fluid testing apparatus as claimed in claim 27 wherein said antibody coated polymeric particles are anti-antigen coated polymeric particles trapped in the membrane.

29. A fluid testing apparatus as claimed in claim 27 wherein said antibody coated polymeric particles are goat anti-mouse antibody coated polymeric particles trapped in the membrane.

30. A method for collecting and testing a biological fluid comprising the steps of:
  a). filling a first container with a ligand having a colored labelling means;
  b). filling a second container positioned adjacent said first container with the biological fluid to be tested;
  c). aliquoting said biological fluid from said second container into said first container by causing said biological fluid to pass through a filter into said first container;
  d). providing relative rotation between said first and second container cutting off biological fluid flow into said first container to provide incubations allowing the formation of said ligand complex;
  e). providing relative rotation between said first and second containers to provide said first container opposite a capillary assembly; and
  f). reacting said ligand complex with antigen mounted to said capillary assembly.

31. A method for collecting and testing a biological fluid as claimed in claim 30, Step d) wherein said relative rotation causes said second container to be positioned at least 90° from its original position during the step c). aliquoting with respect to said first container.

32. A method for collecting and testing a biological fluid as claimed in claim 30, Step e) wherein said relative rotation causes said second container to be positioned at least 180° from its original position during the step c). aliquoting with respect to said first container.

33. A method of collecting and testing a biological fluid comprising the steps of:
  a). filling a first container with a biological fluid to be tested, said first container rotatably mounted in a second container provided with a labelled antibody;
  b). aliquoting the biological fluid into the second container provided with labelled antibody to react with the labelled antibody;
  c). rotating at least one of the containers with respect to the other container to a first position to stop the flow of biological fluid from one container into the other container;
  d). allowing the labelled antibody to complex with specific antigens present in the biological fluid;
  e). rotating at least one of the containers with respect to the other container to a second position, thereby permitting the complexed antigen labelled antibody to enter a capillary assembly mounted to said first container which captures said complexed antigen labelled antibody to provide a test result.

34. A fluid collection and testing apparatus comprising:
  a reaction chamber;
  a collection chamber mounted in relation to and being communicable with said reaction chamber; and
  a capillary test assembly for indicating the presence of at least one predetermined analyte in a fluid, said capillary test assembly being communicable with said reaction chamber.

35. A fluid collection and testing apparatus as claimed in claim 34 wherein said reaction chamber is movable with respect to said collection chamber between first and second positions, whereby fluid present in said collection chamber flows into said reaction chamber in said first position.

36. A fluid collection and testing apparatus as claimed in claim 34 wherein said reaction chamber is movable with respect to said collection chamber between first and second positions, so that fluid present in said reaction chamber flows by capillary action into said capillary test assembly in said second position.

37. A fluid collection and testing apparatus as claimed in claim 34 wherein
  said reaction chamber is movable with respect to said collection chamber between first and second positions whereby fluid present in said collection chamber flows into said reaction chamber in said first position, and
  fluid present in said reaction chamber flows by capillary action into said capillary test assembly in said second position.

38. A fluid collection and testing apparatus as claimed in claim 34 wherein said capillary test assembly includes at least one immobilized reagent for indicating the presence of said at least one predetermined analyte.

39. A fluid collection and testing apparatus as claimed in claim 38 wherein said at least one analyte is at least one specific ligand and said at least one immobilized reagent is capable of forming at least one biospecific complex pair with said at least one specific ligand.

40. A fluid collection and testing apparatus as claimed in claim 38 wherein a visual indicia of the presence of said at least one predetermined analyte is produced by the interaction of said at least one predetermined analyte and said at least one immobilized reagent.

41. A fluid collection and testing apparatus as claimed in claim 40 wherein said at least one immobilized reagent is located in a first region of said capillary assembly and a negative-indicating reagent, indicating the absence of an analyte, is immobilized in a second region of said capillary assembly.

42. A fluid collection and testing apparatus as claimed in claim 41 wherein said negative-indicating reagent comprises a member of a biospecific complex pair.

43. A fluid collection and testing apparatus as claimed in claim 40 wherein the size of area of visual indicia of the presence of said predetermined analyte is related directly to the concentration of analyte originally supplied to said collection chamber.

44. A fluid collection and testing apparatus as claimed in claim 38 wherein one of said at lest one analyte and said at least one immobilized reagent comprises at least one antibody and the other of said at least one analyte and said at least one immobilized reagent comprises at least one antigen.

45. A fluid collection and testing apparatus as claimed in claim 44 wherein one of said at least one antibody and said at least one antigen includes at least one enzyme label.

46. A fluid collection and testing apparatus as claimed in claim 38 wherein said at least one immobilized reagent comprises a plurality of immobilized reagents located in separate zones in said capillary test assembly and each of said plurality of immobilized reagents in capable of interacting only with a different predetermined analyte.

47. A fluid collection and testing apparatus as claimed in claim 34, further including a cap to provide liquid-tight closure of said apparatus.

48. A fluid collection and testing apparatus comprising:
  a reaction chamber; and a housing operatively associated with said reaction chamber and including:

a sample collection chamber communicable with said reaction chamber, and a capillary test assembly for indicating the presence of at least one predetermined analyte in a fluid, said capillary test assembly being attached to said sample collection chamber and communicable with said reaction chamber.

49. A fluid collection and testing apparatus as claimed in claim 48 wherein said reaction chamber is moveable with respect to said sample collection chamber between first and second positions, whereby fluid present in said sample collection chamber flows into said reaction chamber in said first position.

50. A fluid collection and testing apparatus as claimed in claim 48 wherein said reaction chamber is movable with respect to said sample collection chamber between first and second positions, whereby fluid present in said reaction chamber flows by capillary action into said capillary test assembly in said second position.

51. A fluid collection and testing apparatus as claimed in claim 48 wherein, said reaction chamber is movable with respect to said sample collection chamber between first and second positions whereby fluid present in said sample collection chamber flows into said reaction chamber in said first position; and fluid present in said reaction chamber flows by capillary action into said capillary test assembly in said second position.

52. A fluid collection and testing apparatus as claimed in claim 48 wherein said capillary test assembly includes at least one immobilized reagent for indicating the presence of said at least one predetermined analyte.

53. A fluid collection and testing apparatus as claimed in claim 52 wherein at least one analyte is at least one specific ligand and said at least one immobilized reagent is capable of forming at least one biospecific complex pair with said at least one specific ligand.

54. A fluid collection and testing apparatus as claimed in claim 52 wherein a visual indicia of the presence of said at least one predetermined analyte is produced by the interaction of said at least one predetermined analyte and said at least one immobilized reagent.

55. A fluid collection and testing apparatus as claimed in claim 54 wherein said at least one immobilized reagent is located in a first region of said capillary assembly and a negative-indicating reagent, indicating the absence of an analyte is immobilized in a second region of said capillary assembly.

56. A fluid collection and testing apparatus as claimed in claim 55 wherein said negative-indicating reagent comprises a number of a biospecific complex pair.

57. A fluid collection and testing apparatus as claimed in claim 54 wherein the size of area of visual indicia of the presence of said at least one predetermined analyte is related directly to the concentration of analyte originally supplied to said collection chamber.

58. A fluid collection and testing apparatus as claimed in claim 52 wherein one of said at least one analyte and said at least one immobilized reagent comprises at least one antibody and the other of said analyte and said immobilized reagent comprises at least one antigen.

59. A fluid collection and testing apparatus as claimed in claim 58 wherein one of said at least one antibody and said at least one antigen includes at least one enzyme label.

60. A fluid collection and testing apparatus as claimed in claim 52 wherein said at least one immobilized reagent comprises a plurality of immobilized reagents located in separate zones in said capillary test assembly and each of said plurality of immobilized reagents is capable of interacting only with a different predetermined analyte.

61. A fluid collection and testing apparatus as claimed in claim 58, further including a cap to provide liquid-tight closure of said apparatus.

62. A kit for fluid collection and testing for an analyte comprising:

(a) an apparatus for collecting a fluid sample and testing for the presence of an analyte including:
a reaction chamber;
a collection chamber mounted in relation to and being communicable with said reaction chamber;
a capillary test assembly for indicating the presence of at least one predetermined analyte in a fluid and being communicable with said reaction chamber; and (b) at least one test reagent.

63. A kit for fluid collection and testing as claimed in claim 62 wherein said capillary test assembly includes at least one immobilized reagent for indicating the presence of said at least one predetermined analyte.

64. A kit for fluid collection and testing as claimed in claim 62 wherein said at least one test reagent is capable of interacting with said at least one predetermined analyte to form a product which is capable of interacting with said at least one immobilized reagent.

* * * * *